US007713954B2

(12) United States Patent  (10) Patent No.: US 7,713,954 B2
Bonhaus et al. (45) Date of Patent: May 11, 2010

(54) COMPOSITIONS AND METHODS FOR TREATING COGNITIVE DISORDERS

(75) Inventors: Douglas William Bonhaus, Encinitas, CA (US); Renee Sharon Martin, Sunnyvale, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 1119 days.

(21) Appl. No.: 11/241,316

(22) Filed: Sep. 30, 2005

(65) Prior Publication Data

US 2006/0069094 A1  Mar. 30, 2006

Related U.S. Application Data

(60) Provisional application No. 60/614,705, filed on Sep. 30, 2004, provisional application No. 60/630,608, filed on Nov. 24, 2004, provisional application No. 60/707,798, filed on Aug. 12, 2005.

(51) Int. Cl.
*A01N 43/00* (2006.01)
*A01N 43/50* (2006.01)
*A01N 41/10* (2006.01)
*A61K 31/33* (2006.01)
*A61K 31/10* (2006.01)
*C07D 401/04* (2006.01)
*C07D 471/04* (2006.01)
*C07D 487/04* (2006.01)

(52) U.S. Cl. ........................ 514/183; 514/257; 514/396; 514/709

(58) Field of Classification Search .................. 514/183, 514/257, 396, 709
See application file for complete search history.

(56) References Cited

U.S. PATENT DOCUMENTS

| 6,774,241 | B2 | 8/2004 | Clark et al. |
| 6,787,535 | B2 | 9/2004 | Beard et al. |
| 6,790,848 | B2 | 9/2004 | Briggs et al. |
| 6,818,639 | B2 | 11/2004 | Sukhwinder et al. |
| 7,229,984 | B2* | 6/2007 | Harris et al. ........... 514/211.04 |
| 7,312,359 | B2* | 12/2007 | Greenhouse et al. ........ 564/147 |
| 2003/0232825 | A1 | 12/2003 | Berger et al. |
| 2004/0063724 | A1 | 4/2004 | Madera et al. |
| 2004/0087593 | A1 | 5/2004 | Clark et al. |
| 2004/0092512 | A1 | 5/2004 | Maag et al. |
| 2005/0124613 | A1 | 6/2005 | Berger et al. |
| 2005/0165001 | A1 | 7/2005 | Krauss et al. |

(Continued)

FOREIGN PATENT DOCUMENTS

WO WO 01/89498 A2 11/2001

(Continued)

OTHER PUBLICATIONS

Intelihealth, "Alzheimer's disease," online, accessed Jun. 30, 2008, http://www.intelihealth.com/IH/ihtIH/WSIHW000/8303/9117/195703.html?d=dmtHealthAZ.*

(Continued)

*Primary Examiner*—Brandon J Fetterolf
*Assistant Examiner*—Paul Zarek
(74) *Attorney, Agent, or Firm*—David J. Chang (57) ABSTRACT

Methods and pharmaceutical compositions relating to selective antagonists of the 5-HT6 receptor and 5-HT2A receptor useful for the treatment of cognitive disorders are presented.

4 Claims, 3 Drawing Sheets

U.S. PATENT DOCUMENTS

| | | | |
|---|---|---|---|
| 2006/0148820 A1* | 7/2006 | Krauss et al. | 514/254.11 |
| 2006/0154941 A1* | 7/2006 | Huang | 514/266.4 |
| 2006/0167255 A1* | 7/2006 | Greenhouse et al. | 544/329 |
| 2007/0293526 A1* | 12/2007 | New Harris, III | 514/275 |
| 2008/0015208 A1* | 1/2008 | New Harris et al. | 514/275 |
| 2008/0015256 A1* | 1/2008 | Harris et al. | 514/605 |

FOREIGN PATENT DOCUMENTS

| | | |
|---|---|---|
| WO | WO 02/08178 A1 | 1/2002 |
| WO | WO 03/066056 A1 | 8/2003 |
| WO | WO 03/099792 A1 | 12/2003 |
| WO | WO 2006/066790 * | 6/2006 |

OTHER PUBLICATIONS

Burns A and Zaudig M, "Mild cognitive impairment in older people," The Lancet, Dec. 2002, 360(9349), 1963-1965.*

Ebert U and Kirch W, "Scopolamine model of dementia: electroencephalogram findings and cognitive performance," European Journal of Clinical Investigation, Nov. 1998, 28(11), 944-949.*

Garcia-Alloza M, Hirst WD, Chen CP, Lasheras B, Francis PT and Ramirez MJ, "Differential involvement of 5-HT(1B/1D) and 5-HT6 receptors in cognitive and non-cognitive symptoms in Alzheimer's disease," Neuropsychopharmaccology, Feb. 2004, 29(2), 410-416.*

Hook VY, "Neuroproteases in Peptide Neurotransmission and Neurodegenerative Diseases," Biodrugs, 2006, 20(2), 105-119.*

Jelic V, Kivipelto M, and Winblad B, "Clinical trials in mild cognitive impairment: lessons for the future," Journal of Neurology, Neurosurgery and Psychiatry, Apr. 2006, 77(4), 429-438 (Epub Nov. 2005).*

Meneses A, "5-HT system and cognition," Neuroscience and Biobehavioral Reviews, Dec. 1999, 23(98), 1111-1125.*

Meneses A, "Involvement of 5-HT(2A/2B/2C) receptors on memory formation: simple agonism, antagonism, or inverse agonism?" Cellular and Molecular Neuorbiology, Dec. 2002, 22(5-6), 675-688.*

Rosenberg PB and Lyketsos CG, "Mild cognitive impairment: searching for the prodrome of Alzheimer's disease," World Psychiatry, Jun. 2008, 7(2), 72-78.*

Woolley ML, Marsden CA, Sleight AJ, and Fone KC, "Reversal of a cholinergic-induced deficit in a rodent model of recognition memory by the selective 5-HT6 receptor antagonist, Ro 04-6790," Psychopharmacology, Dec. 2003 (Epub 09/20039), 170(4), 358-367.*

American Health Assistance Foundation, http://www.ahaf.org/alzheimers/about/ symptomsandstages.html, accessed Nov. 9, 2009.*

Hedley, L. et al., "The combined effects of the 5-HT$_{2A}$ Antagonist, MDL100,907, and the Selective 5-HT$_6$ Receptor Antagonist, RO4368554, in Rat Models of Psychosis and Cognition," *Behavioral Pharmacology* 16 (2005) S23.

Kennedy, J.S., et al., "A Current review of Olanzapine's Safety in the Geriatric Patent: From Pre-clinical Pharmacology to Clinical Data," *International J. of Geriactric Psychiatry* 16 (2001) S33-S61.

Mori, K., et al. "Effect of Switching to Atypical Antipsychotics on Memory in Patients with Chronic Schizophrenia," *Process in Neuro-Psychopharmacology & Biology Psychiatry* 28 (2004) 659-665.

Russell, M.G.N., et al., "Memories are Made of This (Perhaps): A Review of Serotonin 5-HT$_6$ Receptor Ligands and Their Biological Functions," *Current Topics in Medicinal Chemistry* 2 (2002) 643-654.

* cited by examiner

COMPOSITIONS AND METHODS FOR TREATING COGNITIVE DISORDERS

CROSS REFERENCE TO RELATED INVENTIONS

This application claims the benefit of priority of U.S. Provisional Patent Application Ser. No. 60/614,705 filed Sep. 30, 2004, U.S. Provisional Patent Application Ser. No. 60/630,608 filed Nov. 24, 2004, and U.S. Provisional Patent Application Ser. No. 60/707,798 filed Aug. 12, 2005, which are incorporated herein by reference in their entirety.

FIELD OF THE INVENTION

The claimed invention relates generally to the fields of medicine and medicinal chemistry. More particularly, the invention relates to methods of treating cognitive disorders by inhibition of 5-HT2A and 5-HT6 receptors and compositions therefore.

BACKGROUND

Cognitive and/or degenerative brain disorders are characterized clinically by progressive loss of memory, cognition, reasoning, judgment and emotional stability that gradually leads to profound mental deterioration and ultimately death. In an example of such disorders, Alzheimer's Disease (AD) is a common cause of progressive mental failure (dementia) in aged humans and is believed to represent the fourth most common medical cause of death in the United States. In particular, AD is associated with degeneration of cholinergic neurons in the basal forebrain that play a fundamental role in cognitive functions, including memory (Becker et al., Drug Development Research, 1988, 12, 163-195). Cognitive and degenerative brain disorders have been observed in varied races and ethnic groups worldwide and present a major public health problem. These diseases are currently estimated to affect about two to three million individuals in the United States alone. These diseases are incurable with presently-used medications and will increase worldwide as the human life span increases.

Serotonin receptors have been divided into a number of families and subfamilies (5-HT1 through 5-HT7) and approximately 14 populations have been cloned. One of the newest populations identified is the 5-HT6 subtype. It has been observed that various tricyclic psychotropic agents (neuroleptics, antidepressants, and atypical neuroleptic agents) bind the 5-HT6 receptor with nanomolar affinities (Roth et al., J. Pharmacol. Exp. Ther., 1994, 268, 1403-1410). A rat 5-HT6 receptor was first cloned in 1993 and, more recently, the same group described the cloning of a human 5-HT6 receptor. The 5-HT6 receptors are members of the G-protein superfamily, are positively coupled to an adenylate cyclase second messenger system and are found primarily in the central nervous system. Serotonin bound to the 5-HT6 receptor subgroup activates the adenylate cyclase enzyme, with concomitant increased levels of intracellular cAMP. Although the exact physiological function and clinical significance of the 5-HT6 receptor subgroup is not known, as noted above, many anti-psychotic agents bind these receptors with high affinity. Also, rats that do not express 5-HT6 receptors behave in a manner that seems to involve an increase in cholinergic function.

The 5-HT2A receptor subtype is widely yet discretely expressed in the human brain, including many cortical, limbic, and forebrain regions. This receptor subtype is highly expressed on blood vessel smooth muscle (e.g. aorta and femoral artery) where 5-HT is known to mediate contraction. It is also expressed on mature platelets where it mediates, in part, platelet aggregation, one of the initial steps in the process of vascular thrombosis. Recent studies have shown that antagonism of the 5-HT2A receptor is an alternate molecular mechanism for drugs with antipsychotic efficacy, possibly through antagonism of heightened or exaggerated signal transduction through serotonergic systems. 5-HT2A antagonists are therefore candidates for treating psychosis without extrapyramidal side effects. However, the involvement of the 5-HT2A receptor in cognitive functions is not fully understood and is considered controversial, with studies showing the stimulation of the 5-HT2A receptor to be either cognition-enhancing or impairing (Williams et al., J. Neurosci., 2002, 22, 2843-2854; Harvey, Learn. Mem., 2003, 10, 355-362, Umbricht et al., Neuropsycho-pharmacology, 2003, 28, 170-181).

Atypical antipsychotic drugs such as clozapine or olanzapine, which are non-selective antagonists of the 5-HT6 and 5-HT2A receptors, have been implicated in improving cognitive function but they may also show adverse effects such as delirium and confusion (Mori et al., Prog. Neuropsychopharmacol. Biol. Psychiatry, 2004, 28, 659-665; Kennedy et al., Int. J. Geriatr. Psychology, 2001, 16, S33-S61). However these drugs have been tested only in psychotic patients and their efficacy in improving cognition in non-psychotic patients is not understood.

SUMMARY OF THE INVENTION

It has now been found that the administration of a composition comprising a selective 5-HT6 receptor antagonist and a selective 5-HT2A receptor antagonist is more effective in the treatment of cognitive disorders than the administration of a composition comprising either antagonist alone or a non-selective antagonist. The administration of either a first selective 5-HT6 receptor antagonist compound and a second selective 5-HT2A antagonist compound or a single compound which is a combined selective 5-HT6/5-HT2A receptor antagonist compound requires lower doses to achieve similar or improved efficacy compared to the administration of either antagonist compound alone, and thus may offer additional benefits such as reduced risks of adverse effects, tolerance development, abuse liability, and lack of efficacy.

The present invention therefore relates to a method of treating a disease state associated with a cognitive disorder, and a pharmaceutical composition comprising an effective amount of a composition capable of selectively antagonizing the 5-HT6 receptor and the 5-HT2A receptor. Thus, one aspect of the present invention is a method of treating a disease state associated with a cognitive disorder comprising administering to a subject in need thereof an effective amount of a composition comprising a selective 5-HT6 receptor antagonist and a selective 5-HT2A receptor antagonist, or a combined selective 5-HT6/5-HT2A receptor antagonist.

In another embodiment the invention provides a pharmaceutical composition for treating a disease state associated with a cognitive disorder comprising an effective amount of a composition comprising a selective 5-HT6 receptor antagonist and a selective 5-HT2A receptor antagonist, or a combined selective 5-HT6/5-HT2A receptor antagonist, and a pharmaceutically acceptable excipient.

DETAILED DESCRIPTION OF THE INVENTION

Definitions

The term "selective 5-HT6 receptor antagonist" refers to a compound which binds to and antagonizes the 5-HT6 receptor, acting as either a neutral antagonist or an inverse agonist, and which does not substantially bind to and antagonize other 5-HT receptor subtypes, and does not substantially bind to and antagonize any dopamine receptor subtypes, histamine receptor subtypes or muscarinic receptor subtypes. Lack of "substantial antagonism", as used herein, refers to compounds that bind to off-target receptors with a pKi of about 7 or less. "Off target receptors", as used herein, refers to dopamine receptors (including the various subtypes), histamine receptors (including the various subtypes), muscarinic receptors (including the various subtypes), 5-HT receptors other than 5-HT6 and 5-HT2A receptors, and the like.

The term "target receptor" refers to the receptors 5-HT6 and 5-HT2A, either alone or in combination.

The term "selective 5-HT2A receptor antagonist" refers to a compound which binds to and antagonizes the 5-HT2A receptor, acting as either a neutral antagonist or an inverse agonist, and which does not substantially bind to and antagonize other 5-HT receptor subtypes, and does not substantially bind to and antagonize any other off-target receptor.

The term "combined selective 5-HT6/5-HT2A receptor antagonist" refers to a compound which binds to and antagonizes both 5-HT6 and 5-HT2A receptors, acting as either a neutral antagonist or an inverse agonist, and which does not substantially bind to and antagonize any off-target receptor.

Preferably, a "selective" 5-HT6 and/or 5-HT2A receptor antagonist will exhibit an affinity (pKi) for the target receptor (5-HT6 and/or 5-HT2A) with a value of greater than or equal to about 8 which is at least 30-fold greater than its pKi for the dopamine D2 receptor, the histamine H1 receptor, and the muscarinic M1 and M2 receptors, when measured according to the assays provided below. A "selective" 5-HT6 and/or 5-HT2A receptor antagonist may also exhibit a further selectivity of at least 30-fold greater over the 5-HT2C receptor. Assays that may be used for determining the affinity and selectivity of a 5-HT6 receptor antagonist and/or a 5-HT2A receptor antagonist are well known in the art and are also provided in the Examples below.

The terms "effective amount" and "therapeutically effective amount" refer to a sufficient amount of the agent to provide the desired biological result. That result can be prevention, reduction and/or alleviation of the signs, symptoms, or causes of a disease, or any other desired alteration of a biological system having or at risk of having such signs, symptoms, or disease. An appropriate "effective" amount in any individual case may be determined by one of ordinary skill in the art using routine experimentation.

The term "treating" or "treatment of" a disease state includes: 1) preventing the disease state, i.e. causing the clinical symptoms of the disease state not to develop in a subject that may be exposed to or predisposed to the disease state, but does not yet experience or display symptoms of the disease state; 2) inhibiting the disease state, i.e., arresting the development of the disease state or its clinical symptoms; 3) or relieving the disease state, i.e., causing temporary or permanent regression of the disease state or its clinical symptoms. The term "disease state" refers to any disease, or pathological condition, symptom, disorder, or indication.

The term "subject" refers to mammals and non-mammals which express 5-HT receptors or orthologues of 5-HT receptors. Examples of mammals include, but are not limited to, any member of the Mammalia class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. The term does not denote a particular age or gender.

The terms "cognitive disorder" and "cognitive deficits" indicate disruptions in performance including one or more of the following signs:
1) memory deficits (impaired ability to learn new information or recall previously learned information;
2) one (or more) of the following disturbances:
   a) aphasia (language disturbance)
   b) apraxia (impaired ability to carry out motor activities despite intact motor function)
   c) agnosia (failure to recognize or identify objects despite in tact sensory function)
   d) disturbance in executive functioning (i.e. planning, organizing, sequencing, abstracting);
3) memory disturbances causing significant impairment in social or occupational functioning, and representing a significant decline from a previous level of functioning; and
4) impairment in cognitive functioning as evidenced by neuropsychological testing or quantified clinical assessment, accompanied by objective evidence of a systemic general medical condition or central nervous system dysfunction. Cognitive disorders may include Alzheimer's disease, learning disabilities caused by degenerative disorders, learning disabilities caused by non-degenerative disorders, memory or cognitive dysfunction such as mild cognitive impairment, age-related cognitive decline, cerebral senility, vascular dementia, AIDS-associated dementia, electric shock induced amnesia, memory impairment associated with depression or anxiety, cognitive defects in Parkinson's disease, Down's syndrome, stroke, traumatic brain injury, Huntington's disease, and attention deficit disorder.

The terms "pharmaceutically acceptable" and "pharmacologically acceptable" refer to a material that is useful in preparing a pharmaceutical composition that is generally compatible with the other components of the composition, not deleterious to the recipient, and neither biologically nor otherwise undesirable, and is acceptable for veterinary use as well as human pharmaceutical use. A "pharmaceutically acceptable excipient" as used in the specification and claims includes both one and more than one such excipient.

"Alkyl" means the monovalent linear or branched saturated hydrocarbon moiety, consisting solely of carbon and hydrogen atoms, having from one to twelve carbon atoms. "Lower alkyl" refers to an alkyl group or moiety of one to six carbon atoms, i.e. $C_1$-$C_6$alkyl. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkenylene" means a linear unsaturated divalent hydrocarbon radical of two to six carbon atoms or a branched saturated divalent hydrocarbon radical of three to six carbon atoms, e.g., ethenylene (—CH=CH—), 2,2-dimethylethenylene, propenylene, 2-methylpropenylene, butenylene, pentenylene, and the like.

"Alkoxy" means a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula $R^aR^b$— wherein $R^a$ is alkoxy as defined herein and $R^b$ is alkylene as defined herein. Exemplary alkoxyalkyl moieties include methoxyethyl, ethoxyethyl, 2,3-dimethoxypropyl and the like.

"Alkylcarbonyl" means a moiety of the formula —R'—R", where R' is oxo and R" is alkyl as defined herein.

"Alkylsulfonyl" means a moiety of the formula —R'—R", where R' is —SO$_2$— and R" is alkyl as defined herein.

"Alkylsulfonylalkyl" means a moiety of the formula $R^a$—SO$_2$—$R^b$—, where $R^a$ is alkyl and $R^b$ is alkylene as defined herein. Exemplary alkylsulfonylalkyl groups include, by way of example, 3-methanesulfonylpropyl, 2-methanesulfonylethyl, 2-methanesulfonylpropy, and the like.

"Aminoalkyl" means a group —R—R' wherein R' is amino and R is alkylene as defined herein. "Aminoalkyl" includes aminomethyl, aminoethyl, 1-aminopropyl, 2-aminopropyl, and the like. The amino moiety of "aminoalkyl" may be substituted once or twice with alkyl to provide "alkylaminoalkyl" and "dialkylaminoalkyl" respectively.

"Amidinyl" means a group of the formula:

wherein each R independently is hydrogen or alkyl as defined herein.

"Amidinylalkyl" means a group —R—R' wherein R' is amidinyl as defined herein and R is alkylene.

"Amido" means a group —C(O)—NRR' wherein R and R' each independently is hydrogen or alkyl.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof. "Arylene" means a divalent aryl radical wherein aryl is as defined herein. "Arylene" includes, for example, ortho-, meta- and para-phenylene (1,2-phenylene, 1,3-phenylene and 1,4-phenylene respectively), which may be optionally substituted as defined herein.

"Arylalkyl" and "Aralkyl", which may be used interchangeably, mean a radical —$R^aR^b$ where $R^a$ is an alkylene group and $R^b$ is an aryl group as defined herein; e.g., benzyl, phenylethyl, 3-(3-chlorophenyl)-2-methylpentyl, and the like are examples of arylalkyl.

"Carbamyl means a group of the formula:

wherein $R^x$ and $R^y$ each independently is hydrogen or alkyl.

"Cyanoalkyl" means a moiety of the formula —R'—R", where R' is alkylene as defined herein and R" is cyano or nitrile.

"Cycloalkyl" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof.

"Cycloalkylalkyl" means a moiety of the formula —R'—R", where R' is alkylene and R" is cycloalkyl as defined herein.

"Guanidinyl" as used herein means a group of the formula:

wherein R, R', R" and R'" each independently is hydrogen or alkyl.

"Heteroalkyl" means an alkyl radical as defined herein wherein one, two or three hydrogen atoms have been replaced with a substituent independently selected from the group consisting of —$OR^a$, —$NR^bR^c$, and —$S(O)_nR^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl; and when n is 0, $R^d$ is hydrogen, alkyl, cycloalkyl, or cycloalkylalkyl, and when n is 1 or 2, $R^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Hydroxyalkyl" means a moiety of the formula HO—$R^c$— wherein $R^c$ is alkylene as defined herein. Exemplary hydroxyalkyl moieties include hydroxyethyl, hydroxypropyl, 2,3-dihydroxypropyl and the like.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzoxazolyl, benzoxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof.

"Heteroarylene" means a divalent heteroaryl radical wherein heteroaryl is as defined herein. "Heteroarylene" may be optionally substituted as defined herein. "Heteroarylene" includes, for example, indolylene, pyrimidinylene, and the like.

The terms "halo" and "halogen", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —$CH_2Cl$, —$CH_2CF_3$, —$CH_2CCl_3$, perfluoroalkyl (e.g., —$CF_3$), and the like.

"Haloalkoxy" means a moiety of the formula —OR, wherein R is a haloalkyl moiety as defined herein. Examples of alkoxy moieties include, but are not limited to, methoxy, ethoxy, isopropoxy, and the like.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like.

"Imidazolinyl" as used herein means a group of the formula:

wherein R' is hydrogen or alkyl. Imidazolinyl groups may be optionally substituted as defined herein.

"Imidazolinylalkyl" means a group —R—R' wherein R' is imidazolinyl as defind herein and R is alkylene.

"Imidazolinylaminoalkyl" means a group —R—R'—R" wherein R" is imidazolinyl as defined herein, R' is amino, and R is alkylene. The amino moiety of "imidazolinylaminoalkyl" may be optionally substituted with alkyl.

"Urea" means a group of the formula:

wherein $R^x$, $R^y$ and $R^z$ each independently is hydrogen or alkyl.

"Urealkyl" means a group R—R' wherein R' is urea and R is alkylene.

"Optionally substituted", when used in association with "aryl", "arylene", phenyl", "phenylene", "heteroaryl", heteroarylene or "heterocyclyl", means an aryl, arylene, phenyl, phenylene, heteroaryl, heteroarylene, or heterocyclyl which is optionally substituted independently with one to four substituents, preferably one or two substituents selected from alkyl, cycloalkyl, cycloalkylalkyl, heteroalkyl, hydroxyalkyl, halo, nitro, cyano, hydroxy, alkoxy, amino, acylamino, monoalkylamino, di-alkylamino, haloalkyl, haloalkoxy, heteroalkyl, —COR (where R is hydrogen, alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

General Method

The present invention relates to a method of treating a disease state associated with a cognitive disorder and a pharmaceutical composition comprising an effective amount of a composition comprising a selective 5-HT6 receptor antagonist and a selective 5-HT2A receptor antagonist. The composition comprising a selective 5-HT6 receptor antagonist and a selective 5-HT2A receptor antagonist may comprise a single compound which is a combined selective 5-HT6/5-HT2A receptor antagonist, or a first selective 5-HT6 receptor antagonist compound and a second selective 5-HT2A receptor antagonist compound.

One aspect of the invention is a method for treating a disease state associated with a cognitive disorder, said method comprising administering to a subject in need thereof an effective amount of a pharmaceutical composition that selectively antagonizes the 5-HT6 receptor and the 5-HT2A receptor without substantially antagonizing off-target receptors. In one subgenus of the invention, the pharmaceutical composition comprises a single compound that is a combined selective 5-HT6/2A receptor antagonist. In another subgenus of the invention, the pharmaceutical composition comprises a selective 5-HT6 receptor antagonist compound and a selective 5-HT2A antagonist compound.

Another aspect of the invention is a pharmaceutical composition that selectively inhibits the 5-HT6 receptor and the 5-HT2A receptor without substantially antagonizing the off-target receptors. In one subgenus of the invention, the pharmaceutical composition comprises a single compound that is a combined selective 5-HT6/2A receptor antagonist. In another subgenus of the invention, the pharmaceutical composition comprises a selective 5-HT6 receptor antagonist compound and a selective 5-HT2A antagonist compound.

The compounds of the present invention have shown cognition-enhancing effects in an animal model of cognitive dysfunction as described in detail in Example 4 below. Both the administration of combined selective 5-HT6/2A receptor antagonists and the coadministration of a selective 5-HT6 receptor antagonist together with a selective 5-HT2A receptor antagonist have demonstrated memory improving effects which are statistically significant. These results contrast with the effects in animal cognition models of non-selective 5-HT6 and/or 5-HT2A receptor antagonist compounds, such as olanzapine and clozapine, as reported in the public literature. Several studies have shown treatment with either olanzapine or clozapine resulting in impairment or no effect on memory (Addy and Levin, 2002, Neuropsychopharmacology, 27, 534-541; Skarsfeldt, 1996, Psychopharmacology, 124, 126-133; Rosengarten and Quartermain, 2002, Pharmacol. Biochem. Behav., 2002, 72, 575-579; Rosengarten and Quartermain, 2002, Prog. Neuropsychopharmacol. Biol. Psychiatry, 26, 1047-1054; Terry et al., 2002, Psychopharmacology, 164, 360-368). One study showed improvement in cognitive function by olanzapine but only after a lag time of 14 days (Nowakowska et al., 1999, Pol. J. Pharmacol., 51, 295-300), while another study demonstrated memory improvement by olanzapine and no effect by clozapine (Wolff and Leander, 2003, Psychopharmacology, 168, 410-416).

Compounds known to be combined selective antagonists for both the 5-HT6 and the 5-HT2A receptors are disclosed in the commonly owned U.S. patent applications U.S. Ser. No. 60/424,946 filed on Nov. 8, 2002, and U.S. Pat. No. 7,141,562 filed on Nov. 6, 2003 by Maag et al., entitled "Substituted Benzoxazinones and Uses Thereof"; U.S. Ser. No. 60/537,080 filed on Jan. 16, 2004 by Zhao et al., entitled "Quinazolinone and Benzoxazinone Derivatives and Uses Thereof"; U.S. Ser. No. 60/528,378 filed on Dec. 9, 2003 by Berger et al., entitled "Benzoxazine Derivatives and Uses Thereof"; U.S. Ser. No. 60/568,314 filed on May 5, 2004 by Berger et al., entitled "Arysulfonyl Benzodioxanes, Benzoxazines and Benzothiazines as 5-HT6 Antagonists"; U.S. Ser. No. 60/638,030 filed on Dec. 21, 2004 by Greenhouse et al., entitled "Tetralin and Indane Derivatives and Uses Thereof"; U.S. Ser. No. 60/630,608 filed on Nov. 24, 2004 by Sethofer et al., entitled, "Benzoxazine and Quinoxaline Derivatives and Uses Thereof"; and U.S.Ser. No. 60/699,435 filed on Jul. 13, 2005, by Owens et al., entitled "Benzimidazolone Derivatives and Uses Thereof", all of which are incorporated by reference in full herein. Disclosed compounds are selected from the group consisting of Formula I, Formula II, Formula III, Formula IV, Formula V, Formula VI, and Formula VII:

Formula I

Formula II

Formula III

-continued

Formula IV

Formula V

Formula VI

Formula VII wherein
Y is C or S;
m is 1 when Y is C and m is 2 when Y is S;
n is 1 or 2;
p is from 0 to 3;
q is from 1 to 3;
t is from 1 to 3;
u is from 0 to 3;
v is from 1 to 3;
w is from 0 to 4;
x is 0 or 1;
y is from 1 to 4;
Z is —(CR$^a$R$^b$)$_r$— or —SO$_2$—, wherein r is from 0 to 2 and each of R$^a$ and R$^b$ is independently hydrogen or alkyl;
X is CH or N;
A is —NR$^3$— or —O— wherein R$^3$ is: hydrogen; alkyl, acyl, amidoalkyl, hydroxyalkyl or alkoxyalkyl;
Ar is optionally substituted aryl or optionally substituted heteroaryl;
G is —O—, —S— or —NR$^e$— wherein R$^e$ is hydrogen, alkyl, alkylcarbonyl or alkylsulfonyl;
J is a bond, —C(=O)—, or —SO$_2$—;
each R$^1$ independently is: halo, alkyl, haloalkyl, heteroalkyl, alkoxy, cyano, —S(O)$_s$—R$^c$, —C(=O)—NR$^c$R$^d$, —SO$_2$—NR$^c$R$^d$, —N(R$^c$)—C(=O)—R$^d$, or —C(=O)R$^c$, wherein s is from 0 to 2 and each of R$^c$ and R$^d$ is independently hydrogen or alkyl;

R$^2$ is: aryl or heteroaryl;
each of R$^4$ and R$^5$ is independently hydrogen or alkyl, or one of R$^4$ and R$^5$ together with R$^3$ and the atoms therebetween or with their shared carbon may form a ring of 3 to 7 members that optionally includes a nitrogen or oxygen heteroatom;
each of R$^6$, R$^7$, R$^8$, R$^9$ and R$^{10}$ is independently hydrogen or alkyl, or one of R$^6$ and R$^7$ together with R$^{10}$ and the atoms to which they are attached may form a cycloalkyl ring of 3 to 7 members, or of R$^6$ and R$^7$ together with the atoms to which they are attached may form a cycloalkyl ring of 3 to 7 members, or one of R$^6$ and R$^7$ together with one of R$^8$ and R$^9$ and the atoms to which they are attached may form a cycloalkyl ring of 3 to 7 members;
R$^{11}$ and R$^{12}$ each independently is hydrogen, alkyl or cycloalkyl, or one of R$^{11}$ and R$^{12}$ is hydrogen or alkyl and the other is a four or five-membered heteroaryl or heterocyclyl that contains one or two nitrogen atoms, or R$^{11}$ and R$^{12}$ together with the nitrogen to which they are attached may form a four, five or six-membered ring that optionally contains an additional heteroatom selected from N, O and S, or R$^{11}$ and R$^{12}$ together with the nitrogen to which they are attached may form a guanidinyl or imidazolyl group;
each R$^{13}$ is independently alkyl, hydroxyalkyl or alkoxyalkyl, or two of R$^{13}$ together with the atoms to which they are attached may form a carbocyclic ring of four to six members, or one of R$^{13}$ together with one of R$^{11}$ and R$^{12}$ and the atoms to which they are attached may form a five or six-membered ring;
R$^{14}$ and R$^{15}$ each independently is hydrogen or alkyl, or one of R$^{14}$ and R$^{15}$ together with one of R$^{11}$ and R$^{12}$ and the atoms to which they are attached may form a five or six-membered ring;
each R$^{16}$ is independently halo, alkyl, haloalkyl, cyano, —SO$_2$R$^f$, —C(=O)—NR$^g$R$^h$, —SR$^g$, —C(=O)—R$^g$, wherein each R$^f$, R$^g$ and R$^h$ and is independently hydrogen or alkyl;
R$^{17}$ and R$^{18}$ each independently is hydrogen or alkyl, or R$^{17}$ and R$^{18}$ together may form =NR$^i$ wherein R$^i$ is hydrogen or alkyl;
R$^{19}$ and R$^{20}$ each independently is hydrogen or alkyl, or one of R$^{19}$ and R$^{20}$ is hydrogen and the other is an optionally substituted heteroaryl, or R$^{19}$ and R$^{20}$ together with the nitrogen to which they are attached may form an amidinyl group, a urea group, a guanidinyl group, or a five- or six-membered ring that optionally includes an additional heteroatom selected from O, N and S, or one of R$^{19}$ and R$^{20}$ and one of R$^{17}$ and R$^{18}$ together with the atoms to which they are attached may form a five- or six-membered ring that optionally includes an additional heteroatom selected from O, N and S;
R$^{21}$ and R$^{22}$ each independently is hydrogen or alkyl, or R$^{21}$ and R$^{22}$ together with the carbon atom to which they are attached may form a carbocyclic ring of four to six members;
R$^{23}$ and R$^{24}$ each independently is hydrogen or alkyl;
R$^{25}$ and R$^{26}$ each independently is hydrogen, alkyl, —(C=NR$^j$)—NR$^k$R$^m$, or —(CH$_2$)$_2$—NR$^k$R$^m$ wherein R$^j$, R$^k$ and R$^m$ each independently is hydrogen or alkyl, or R$^{25}$ and R$^{26}$ together with the nitrogen to which they are attached may form a four, five or six-membered ring that optionally includes an additional heteroatom selected from O, N and S, or one of $R^{25}$ and $R^{26}$ together with one of $R^{23}$ and $R^{24}$ together with the atoms to which they are attached may form a ring of four to six members;

$X_1$ is —$NR^n$—, —O—, —S—, —$CR^oR^p$—, or —C(O)— wherein $R^n$ is hydrogen or alkyl, $R^o$ is hydrogen, fluoro or alkyl, $R^p$ is hydrogen, fluoro, alkyl, hydroxy, or alkoxy, or $R^o$ and $R^p$ together with the atom to which they are attached may form a three to six-membered optionally substituted ring that optionally includes a heteroatom selected from O, N and S;

$Y_1$ is —O—, —$NR^q$—, or —$CR'R^s$—, wherein $R^q$, $R^r$ and $R^s$ each independently is hydrogen or alkyl;

$R^{27}$ and $R^{28}$ each independently is hydrogen or alkyl;

$R^{29}$ and $R^{30}$ each independently is hydrogen or alkyl, or $R^{29}$ and $R^{30}$ together with the nitrogen to which they are attached may form a four to seven-membered optionally substituted ring that optionally includes an additional heteroatom selected from O, N and S, or one of $R^{29}$ and $R^{30}$ and one of $R^{27}$ and $R^{28}$ together with the atoms to which they are attached may form a four to seven-membered optionally substitued ring that optionally includes an additional heteroatom selected from O, N and S, or one of $R^{29}$ and $R^{30}$ together with $R^q$ and the atoms to which they are attached may form a four to seven-membered optionally substituted ring that optionally includes an additional heteroatom selected from O, N and S, or one of $R^{29}$ and $R^{30}$ and one of $R^r$ and $R^s$ together with the atoms to which they are attached may form a four to seven-membered ring that optionally includes an additional heteroatom selected from O, N and S;

and the pharmaceutically acceptable acid addition salts thereof.

Preferred compounds in the present invention are the exemplary compounds selected from the group consisting of Formula I, Formula II, Formula III, Formula IV, Formula V, Formula VI, and Formula VII in which Y is C, m is 1, n is 1, q is 2, t is 1, u is 0, G is —O—, X is N, and $R^6$, $R^7$, $R^8$, $R^9$, $R^{10}$, $R^{14}$, $R^{15}$, $R^{17}$, $R^{18}$, $R^{21}$, $R^{22}$ are all hydrogen, for example the following compounds:

(1) 4-benzyl-6-methyl-8-piperazin-1-yl-4H-benzo[1,4]oxazin-3-one,
(2) 4-(3-chloro-benzyl)-6-methoxy-8-piperazin-1-yl-4H-benzo[1,4]oxazin-3-one,
(3) 4-benzyl-8-piperazin-1-yl-4H-benzo[1,4]oxazin-3-one,
(4) 4-(4-fluoro-benzyl)-6-fluoro-8-piperazin-1-yl-4H-benzo[1,4]oxazin-3-one,
(5) 4-(3-chloro-benzyl)-6-fluoro-8-piperazin-1-yl-4H-benzo[1,4]oxazin-3-one,
(6) 4-(3-Fluoro-benzyl)-2,2-dimethyl-8-piperazin-1-yl-4H-benzo[1,4]oxazin-3-one,
(7) 4-(3-Chloro-benzyl)-2,2-dimethyl-8-piperazin-1-yl-4H-benzo[1,4]oxazin-3-one,
(8) 4-Benzyl-6-fluoro-2,2-dimethyl-8-piperazin-1-yl-4H-benzo[1,4]oxazin-3-one,
(9) 4-Benzyl-2,2,6-trimethyl-8-piperazin-1-yl-4H-benzo[1,4]oxazin-3-one,
(10) 4-(3-Fluoro-benzyl)-2,2,6-trimethyl-8-piperazin-1-yl-4H-benzo{1,4}oxazin-3-one,
(11) 1-(3-Fluoro-benzyl)-5-piperazin-1-yl-1,4-dihydro-benzo[d][1,3]oxazin-2-one,
(12) 1-(3-Fluoro-benzyl)-7-methyl-5-piperazin-1-yl-3,4-dihydro-1H-qinazolin-2-one
(13) 6-Fluoro-4-(3-fluoro-benzyl)-2,2-dimethyl-8-piperazin-1-yl-4H-benzo[1,4]oxazin-3-one,
(14) 6-Fluoro-4-(4-fluoro-benzyl)-2,2-dimethyl-8-piperazin-1-yl-4H-benzo[1,4]oxazin-3-one,
(15) 4-(3-Chloro-benzyl)-6-fluoro-2,2-dimethyl-8-piperazin-1-yl-4H-benzo[1,4]oxazin-3-one,
(16) 1-(3-Chloro-benzyl)-5-piperazin-1-yl-3,4-dihydro-1H-quinazolin-2-one,
(17) 1-(3,4-Difluoro-benzyl)-5-piperazin-1-yl-3,4-dihydro-1H-quinazolin-2-one,
(18) 1-(3-Fluoro-benzyl)-5-piperazin-1-yl-3,4-dihydro-1H-quinazolin-2-one,
(19) 1-(4-Fluoro-benzyl)-5-piperazin-1-yl-3,4-dihydro-1H-quinazolin-2-one,
(20) 1-(4-Chloro-benzyl)-5-piperazin-1-yl-3,4-dihydro-1H-quinazolin-2-one,
(21) 1-(3-Fluoro-benzyl)-7-methyl-5-piperazin-1-yl-3,4-dihydro-1H-quinazolin-2-one,
(22) 4-(3-Fluoro-phenylsulfonyl)-2,2-dimethyl-8-piperazin-1-yl-3,4-dihydro-2H-benzo[1,4]oxazine,
(23) 4-(3-Chloro-phenylsulfonyl)-2,2-dimethyl-8-piperazin-1-yl-3,4-dihydro-2H-benzo[1,4]oxazine,
(24) 6-Fluoro-4-(2-fluoro-phenylsulfonyl)-2,2-dimethyl-8-piperazin-1-yl-3,4-dihydro-2H-benzo[1,4]oxazine,
(25) 6-Fluoro-4-(3-fluoro-phenylsulfonyl)-2,2-dimethyl-8-piperazin-1-yl-3,4-dihydro-2H-benzo[1,4]oxazine,
(26) 6-Fluoro-4-(4-fluorophenylsulfonyl)-2,2-dimethyl-8-piperazin-1-yl-3,4-dihydro-2H-benzo[1,4]oxazine,
(27) [7-(3-Fluoro-phenylsulfonyl)-2,3-dihydro-benzo[1,4]dioxin-2-(R)-ylmethyl]-methyl-amine,
(28) C-[7-(3-Fluoro-phenylsulfonyl)-2,3-dihydro-benzo[1,4]dioxin-2-(S)-yl]-methylamine,
(50) (7-Phenylsulfonyl-1,2,3,4-tetrahydro-naphthalen-1-ylmethyl)-(5,5-dimethyl-1,4,5,6-tetrahydro-pyrimidin-2-yl)-amine,
(51) (6-Phenylsulfonyl-1,2,3,4-tetrahydro-naphthalen-1-ylmethyl)-(4,5-dihydro-1H-imidazol-2-yl)-amine,
(52) N-(6-Phenylsulfonyl-1,2,3,4-tetrahydro-naphthalen-1-ylmethyl)-guanidine,
(53) 3-(6-Phenylsulfonyl-1,2,3,4-tetrahydro-naphthalen-1-yl)-propionamidine,
(54) C-(6-Phenylsulfonyl-1,2,3,4-tetrahydro-naphthalen-1-yl)-methylamine,
(55) (6-Phenylsulfonyl-1,2,3,4-tetrahydro-naphthalen-1-ylmethyl)-methyl-amine,
(56) N-(6-Phenylsulfonyl-1,2,3,4-tetrahydro-naphthalen-1-ylmethyl)-acetamidine,
(57) 2-[6-(2-Fluoro-phenylsulfonyl)-1,2,3,4-tetrahydronaphthalen-1-yl]-ethylamine,
(58) 6-Phenylsulfonyl-4-piperidin-4-yl-3,4-dihydro-2H-benzo[1,4]oxazine,
(59) 1-(7-Phenylsulfonyl-2,3-dihydro-benzo[1,4]oxazin-4-yl)-2-(4,5-dihydro-1H-imidazol-2-yl)-ethanone,
(60) 7-Phenylsulfonyl-4-piperidin-4-yl-3,4-dihydro-2H-benzo[1,4]oxazine,
(61) 7-Phenylsulfonyl-4-pyrrolidin-3-yl-3,4-dihydro-2H-benzo[1,4]oxazine,
(62) 1-Benzyl-4-piperazin-1-yl-1,3-dihydro-benzoimidazol-2-one,
(63) 1-Benzyl-4-(2-methylamino-ethoxy)-1,3-dihydro-benzoimidazol-2-one, and
(64) 1-Benzyl-4-piperazin-1-yl-1,3-dihydro-benzoimidazol-2-one;

or pharmaceutically acceptable acid addition salts thereof.

The composition comprising a selective 5-HT6 receptor antagonist and a selective 5-HT2A receptor antagonist of the present invention may also comprise a first compound which is a selective 5-HT6 receptor antagonist compound and a second compound which is a selective 5-HT2A receptor antagonist compound.

Compounds known to be selective 5-HT6 receptor antagonist compounds include indole derivatives of the type described in US 2003/0073700, benzoxazine derivatives of the type described in US 2003/0232825 and in U.S. Ser. No. 60/528,378,4-piperazinylindoles of the type described in US 2003/0045527, 4-piperazinyl benzenesulfonyl indoles of the type described in US 2004/0087593, 1-sulfonyl-4-aminoalkoxy indoles of the type described in US 2003/0229069, and 2-7 substituted indoles of the type described in US 2004/0063724, all of which are incorporated by reference herein. Presently preferred compounds include:

(29) 3-phenylsulfonyl-1-methyl-5-piperazin-1-yl-1H-indole,
(30) 3-(3-chloro-phenylsulfonyl)-7-piperazin-1-yl-1H-indole,
(31) 3-(2,3-dichloro-phenylsulfonyl)-1-methyl-5-piperazin-1-yl-1H-indole,
(32) 3-phenylsulfonyl-7-(4-methyl-piperazin-1-yl)-1H-indole,
(33) 3-(4-chloro-phenylsulfonyl)-5-piperazin-1-yl-1H-indole,
(34) 3-(3,5-dichloro-phenylsulfonyl)-5-piperazin-1-yl-1H-indole,
(35) 3-(3-chloro-phenylsulfonyl)-7-(4-methyl-piperazin-1-yl)-1H-indole;
(36) 4-(2,3-dichloro-phenylsulfonyl)-8-piperazin-1-yl-3,4-dihydro-2H-benzo[1,4]oxazine,
(37) 4-(2-fluoro-phenylsulfonyl)-8-piperazin-1-yl-3,4-dihydro-2H-benzo[1,4]oxazine,
(38) 6-chloro-4-(2-fluoro-phenylsulfonyl)-8-piperazin-1-yl-3,4-dihydro-2H-benzo[1,4]oxazine,
(39) 6-chloro-4-(naphthalene-1-sulfonyl)-8-piperazin-1-yl-3,4-dihydro-2H-benzo[1,4]oxazine,
(40) 6-chloro-4-(2,3-dichloro-phenylsulfonyl)-8-piperazin-1-yl-3,4-dihydro-2H-benzo[1,4]oxazine;
(41) 1-(naphthalene-1-sulfonyl)-4-piperazin-1-yl-1H-indole,
(42) 1-phenylsulfonyl-4-piperazin-1-yl-1H-indole,
(43) 1-(2,5-dichloro-phenylsulfonyl)-4-piperazin-1-yl-1H-indole,
(44) 1-(3-fluoro-phenylsulfonyl)-4-piperazin-1-yl-1H-indole,
(45) 1-(3-chloro-phenylsulfonyl)-4-piperazin-1-yl-1H-indole,
(46) 1-(2-fluoro-phenylsulfonyl)-4-piperazin-1-yl-1H-indole,
(47) 1-phenylsulfonyl-3-bromo-4-piperazin-1-yl-1H-indole,
(48) (7-phenylsulfonyl-2,3-dihydro-benzo[1,4]dioxin-2-(R)-ylmethyl)-methyl-amine,
(49) [7-(3-fluoro-phenylsulfonyl)-2,3-dihydro-benzo[1,4]dioxin-2-(S)-ylmethyl]-methyl-amine;

or pharmaceutically acceptable acid addition salts thereof.

Other compounds known to be selective 5-HT6 receptor antagonist compounds include 4-amino-N-(2,6-bis-methylamino-pyrimidin-4-yl)-benzenesulfonamide (Ro 04-6790) and 4-amino-N-(2,6bis-methylamino-pyridin-4-yl)-benzenesulphonamide (Ro 63-0563) described in EP 0815861 incorporated by reference herein; 5-chloro-N-(4-methoxy-3-piperazin-1-yl-phenyl)-3-methyl-2-benzothiophenesulfonamide (SB271046) and N-[4-Methoxy-3-(4-methyl-1-piperazinyl)-phenyl]-5-chloro-3-methylbenzo-thiophene-2-yl sulphonamide (SB258510) described in WO 98/27081 incorporated by reference herein; N-(2,5-dibromo-3-fluorophenyl)-4-methoxy-3-piperazin-1-ylbenzenesulfonamide (SB357134) described in WO 99/02502 incorporated by reference herein.

Compounds known to be selective 5-HT2A receptor antagonist compounds are, for example, R-α-(2,3-dimethoxyphenyl)-1-[2-(4-fluorophenyl)ethyl]-4-piperidinemethanol (MDL-100907), described in WO 91/18602 incorporated by reference herein; and (1Z,2E)-1-(2-fluorophenyl)-3-(4-hydroxyphenyl)prop-2-en-1-one-O-(2-dimethylaminoethyl) oxime (SR 46349B), described in EP 0373998, incorporated by reference herein.

Any reference herein to the compound specifically named above includes also the pharmaceutically acceptable acid addition salts thereof.

Administration and Pharmaceutical Composition

The present invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the present invention will be administered in a therapeutically effective amount by any of the accepted modes of administration for agents that serve similar utilities. Suitable dosage ranges are typically about 1-500 mg daily, preferably about 1-100 mg daily, and most preferably about 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral, using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may comprise conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxy-methylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, nitrogen, nitrous oxide, carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinyl-pyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacyclo-heptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa.

EXAMPLES

Example 1

Determining Affinity at Human 5-HT6 Receptors

Ligand affinity at 5-HT6 receptors was determined using competition binding with [$^3$H]-Lysergic Acid Diethylamide (LSD) at membranes derived from HEK-293 cells recombinantly expressing human 5-HT6. In brief, cell membranes prepared by homogenization from HEK293-h5-HT6 cells were incubated with 2.2 nM [$^3$H]-LSD and a range of concentrations of non-labeled test compound for 75 minutes at 37° C. Data were analyzed by non-linear regression to logistic equation (1), and ligand affinity was determined by converting $IC_{50}$ values so obtained to Ki using the Cheng-Prusoff equation (2) (Cheng & Prusoff, 1973). The affinity of [$^3$H]-LSD determined from separate saturation binding experiments in these membranes was 2.2 nM.

$$\text{bound radioactivity} = \min + \frac{(\max - \min)[A]}{IC_{50} + [A]} \quad \text{Equation (1)}$$

Where min and max are the levels of displaceable binding due to the zero and maximal concentrations of unlabelled competitor, A, respectively, $IC_{50}$ is the midpoint of the curve and Hill slope is constrained to unity (as it is found not to vary significantly from this value).

$$IC_{50} = K_I \left(1 + \frac{L^*}{K_D}\right) \quad \text{Equation (2)}$$

where the affinity of [$^3$H]-LSD, $K_D$, was previously determined by saturation binding experiments to be 2.2 nM, L* is the concentration of [$^3$H]-LSD used (2.2 nM), and $K_1$ is the affinity of the unlabelled compound as derived from its $IC_{50}$ determined experimentally.

All test and control compounds were dissolved in 100% DMSO at 10 mM and diluted as indicated in aqueous assay buffer. $K_1$ values are presented at the mean and standard deviation of 3 separate determinations each consisting of the compound tested at each concentration in duplicate.

Example 2

Determining Function at Human Recombinant 5-HT$_6$, 5-HT$_{2A}$ and 5-HT$_{2C}$ Receptors The effect of test compound on the function of human 5-HT$_6$, human 5-HT$_{2A}$ and human 5-HT$_{2C}$ receptors was determined by measurement of changes in intracellular calcium using a fluorescent calcium dye (Fluo3-AM). Fluorescence was imaged on the Fluorescent Light Imaging Plate Reader (FLIPR, Molecular Devices). Changes in fluorescence due to test compound, administered on its own (for assessment of agonist efficacy) or in the presence of 5-HT (for assessment of antagonist potency) were made in HEK293 cells stably expressing human recombinant 5-HT$_6$ receptor fused to Gα16, or CHO-K1 cells stably expressing human recombinant 5-HT$_{2A}$ or human recombinant 5-HT$_{2C}$ receptors.

In all cases, cells were seeded 12-24 hours prior to the experiment on poly-D-Lysine coated 96-well black/clear plates in DMEM or F12 cell culture media supplemented with 10% Fetal Bovine Serum. Culture media was removed by 4×300 µl exchanges of surrounding media with Hanks balanced salts solution containing 10 mM HEPES, 2 mM CaCl$_2$ and 2.5 mM probenecid using an EL405 96-well plate washer. Cells were incubated 1 hour at 37° C. with the calcium sensitive dye, Fluo-3 AM (2.2 µg/ml). At the end of the incubation, extracellular dye was removed by washing in the HEPES buffer described above. Test compound was administered into different wells over a range of concentrations ($10^{-5}$-$10^{-10}$ M), and response recorded for 1.5 minutes as a change in fluorescence counts. At the end of this interval 5-HT (10 nM for 5-HT$_6$ or 5-HT$_{2A}$, or 1 nM for 5-HT$_{2C}$) was added to all wells. All test and control compounds were dissolved in 100% DMSO at 10 mM and diluted as indicated in aqueous assay buffer.

Antagonist potency was determined by non-linear regression analysis of the data for concentration-dependent inhibition of response to 5-HT using logistic equation (3)

$$\text{Fluorescence counts} = \frac{(\max)[A]}{IC_{50} + [A]} \quad \text{Equation (3)}$$

where max is the response to 5-HT in the absence of antagonist, A, $IC_{50}$ is the midpoint of the curve and Hill slope is constrained to unity. Note that background fluorescence is subtracted prior to non-linear regression.

All determinations were made in duplicate. All changes in fluorescence were detected in the FLIPR 96 with an excitation wavelength of 488 nM, 0.3 watts and emission detected between 510 and 560 nM with a camera exposure of 0.4 sec. Responses are presented as a percentage of the within-well response to ionomycin (5 µM), administered at the end of all agonist and antagonist additions.

Example 3

Affinity Determination at the Dopamine D2, Histamine H1, Muscarinic M1 and M2 Receptors Ligand binding affinities at the Dopamine D2 receptor were determined using human recombinant D2 receptor as described in Grandy et al., Proc. Natl. Acad. Sci., 1989, 86, 9762-9766. Affinities to the Histamine H1 receptor were determined using guinea-pig cerebellum as described in Dini et al., Agents and Actions, 1991, 33, 181-184. Binding affinities at Muscarinic M1 and M2 receptors were determined using human recombinant M1 and M2 receptors, according to the procedures described in Dorje et al., 1991, J. Pharmacol. Exp. Ther., 256, 727-733.

The affinity estimates of several exemplary compounds at various receptors are compared to those of the non-selective 5-HT6/5-HT2A receptor antagonist compounds, Olanzapine and Clozapine, and are summarized in Table 1.

TABLE 1

| Receptor Affinity (pKi) | 5-HT6 | 5-HT2A | 5-Ht2C | Dopamine D2 | Histamine H1 | Muscarinic M1 | Muscarinic M2 |
|---|---|---|---|---|---|---|---|
| Cmpd 3 | 9.8 | 8.9 | 7.2 | <6 | <6 | <6 | <6 |
| Cmpd 18 | 9.2 | 8.7 | 7.2 | <6 | <6 | <6 | <6 |
| Cmpd 32 | 9.5 | 7.1 | 6.8 | <6 | <6.5 | <6.5 | <6.5 |
| Cmpd 52 | 8.9 | 6.1 | 6.0 | <6 | <6 | <6 | <6 |
| Cmpd 64 | 9.6 | 7.6 | 6.2 | <6 | <6.5 | 6.7 | <6.5 |
| SR46349B | <6 | 9.0 | 7.0 | <6 | <6 | <6.5 | <6 |
| Olanzapine | 8.6 | 8.6 | 7.5 | 7.7 | 8.2 | 8.7 | 7.7 |
| Clozapine | 8.4 | 8.2 | 7.4 | 6.9 | 8.2 | 8.7 | 8.0 |

Example 4

Novel Object Recognition Model

Twenty-four 5-month-old male Wistar rats were used. The animals were housed individually in standard Makrolon cages on sawdust bedding in an air-conditioned room (about 20° C.). They were kept under a 12/12-hour light/dark cycle (lights on from 18.00 to 6.00 h) and had free access to food and water. Rats were housed and test in different rooms. A radio, which was playing softly, provided background noise in all rooms. All testing was done between 9.00 and 16.00 h.

Scopolamine hydrobromide was prepared daily and dissolved in saline. Scopolamine HBr was tested at 0 and 0.1 mg/kg (n=24 per dose), administered i.p. (injection volume 1 ml/kg) 30 minutes before trial 1. Test compounds were prepared daily and dissolved in saline, and the pH was adjusted to pH 5-7 using (0.1 N) NaOH. The compounds were administered orally or i.p. over a range of doses to n=12-24 animals per dose (injection volume 1 ml/kg). Time of dosing prior to first trial (T1) can be chosen to match the expected plasma Cmax for the compound. Administration was always given i.p. (injection volume 1 ml/kg).

The object recognition test was performed as described by Ennaceur and Delacour, Behav. Brain Res., 1988, 31, 47-59. This test measures the memory of an animal, by testing the ability of the animal to recognize that there is a new object in its environment. The apparatus consisted of a circular arena, 83 cm in diameter. Half of the 40 cm high wall was made of gray polyvinyl chloride, the other half of transparent polyvinyl chloride. The light intensity was equal in the different parts of the apparatus. Two objects were placed in a symmetrical position about 10 cm away from the gray wall. Each object was available in triplicate. Four different sets of objects were used: 1) a cone consisting of a gray polyvinyl chloride base (maximal diameter 18 cm) with a brass collar on top (total height 16 cm), 2) a standard 1 l transparent glass bottle (diameter 10 cm, height 22 cm) filled with sand, 3) a massive metal block (10.0×5.0×7.5 cm) with two holes (diameter 1.9 cm), and 4) a massive aluminum block with a tapering top (13.0×8.0×8.0 cm). A rat could not displace the objects. Fluorescent red tubes and a light bulb provided a constant illumination of about 20 lux on the floor of the apparatus.

A testing session comprised two trials. The duration of each trial was 3 min. During the first trial (T1) the apparatus contained two identical objects (samples). A rat was always placed in the apparatus facing the wall at the middle of the front (transparent) segment. After the first exploration period the rat was put back in its home cage. Subsequently, after a predetermined delay interval, the rat was put back in the apparatus for the second trial (T2), but now with two dissimilar objects, a familiar one (the sample) and a new object. The times spent in exploring each object during T1 and T2 were recorded manually with a personal computer. "Exploration" was defined as directing the nose to the object at a distance of no more than 2 cm and/or touching the object with the nose. Sitting on the object was not considered as exploratory behavior. In order to avoid the presence of olfactory trails the objects were always thoroughly cleaned. All combinations and locations of objects were used in a balanced manner to reduce potential biases due to preferences for particular locations or objects.

In the first week, the animals were handled daily and were adapted to the procedure in three days, i.e. they were allowed to explore the apparatus (without any objects) twice for 5 min each day. The rats were also adapted to the i.p. injection by a saline injection (0.5 ml) 30 min before the first exploration trial.

Figure 1:
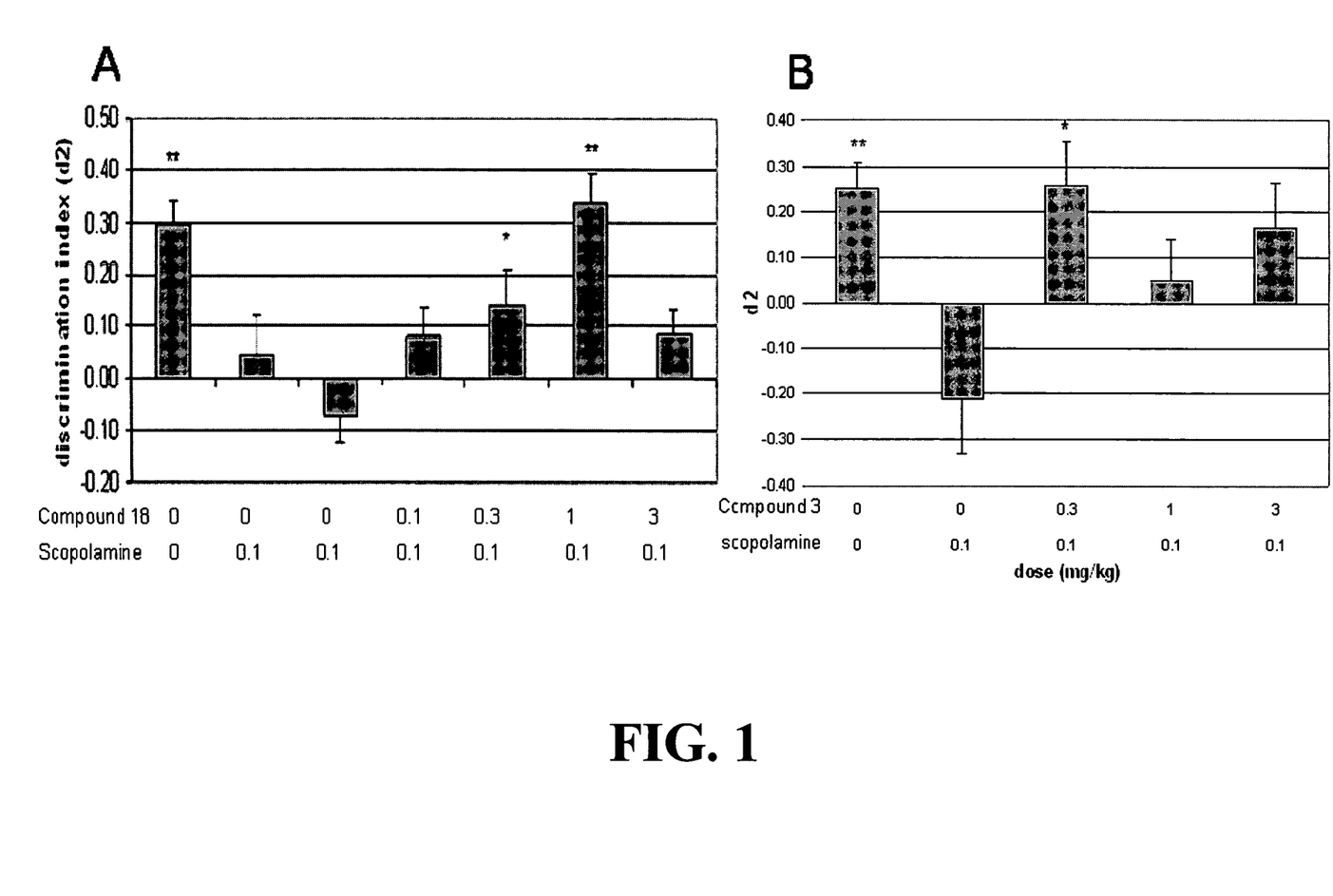
FIG. 1 shows the effect of Compound 18 (A) or Compound 3 (B) on the discrimination performance in an object recognition task investigated in 5-month-old male rats whose performance in this task was disrupted by administration of scopolamine.

FIG. 1 shows the results of this study using two combined selective 5-HT6/5-HT2A receptor antagonist compounds, Compound 18 (A) and Compound 3 (B). Rats were treated with Compound 18 (0.3, 1, 3 mg/kg po) or Compound 3 (0.1, 0.3, 1 and 3 mg/kg i.p.) 90 or 60 mins prior to administration of scopolamine (0.1 mg/kg ip). The time each animal spent investigating the novel and familiar objects in the arena during a over a 3 min interval, commencing 30 minutes after the administration of scopolamine, was scored. The discrimination index (d2) was calculated from $(b-a)/(a+b)$, where a and b are the time spent exploring the familiar and novel objects, respectively. Data were analyzed by Anova. Data are presented as means+S.E.M, (* $P<0.05$; ** $P<0.01$). Treatment with Compound 18 at 0.3 mg/kg and 1 mg/kg doses and with Compound 3 at 0.3 mg/kg dose showed statistically significant reversal of the memory impairment induced by scopolamine.

Figure 2:
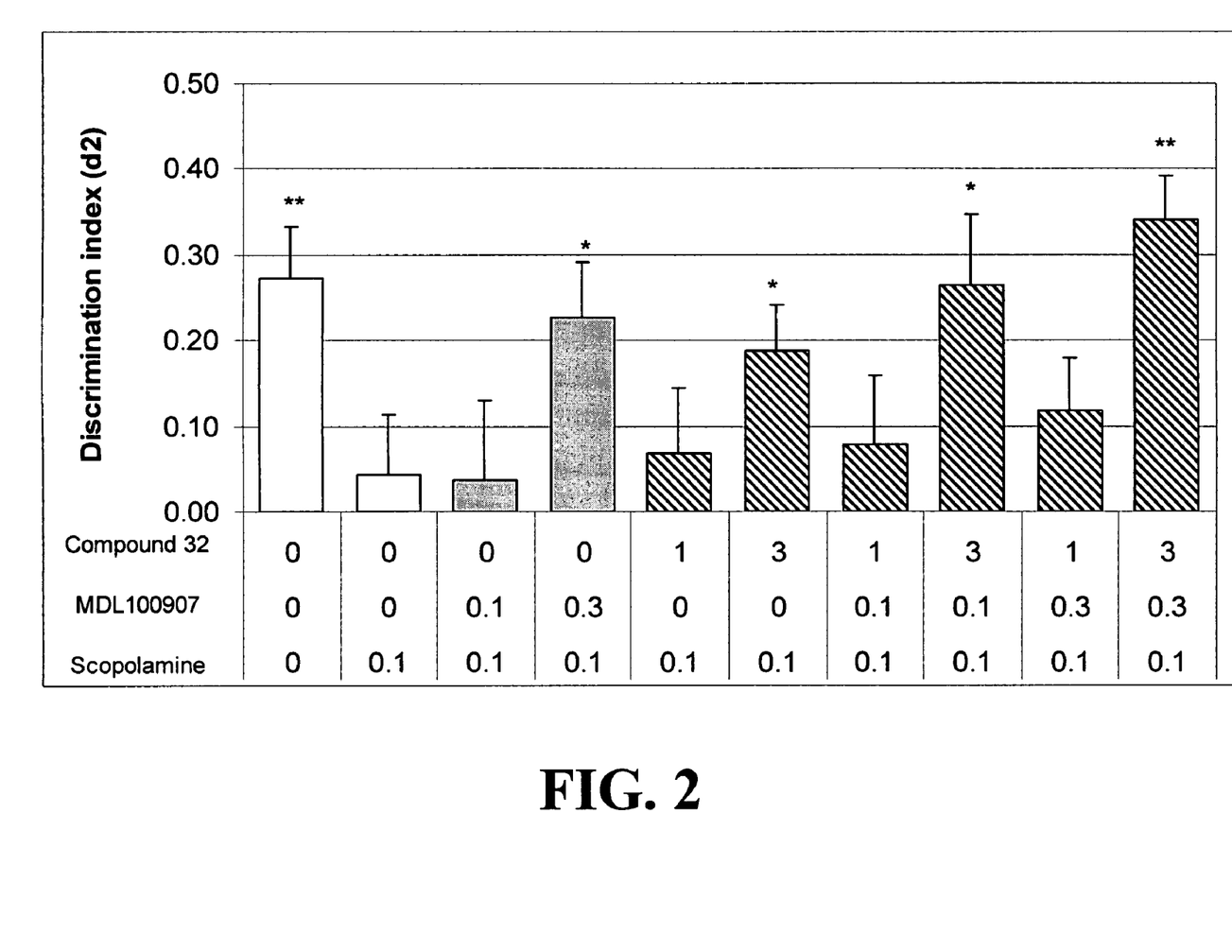
FIG. 2 shows the effect of coadministered selective 5-HT2A antagonist (MDL-100907) and selective 5-HT6 antagonist (Compound 32) on the discrimination performance in an object recognition task investigated in 5-month-old male rats whose performance in this task was disrupted by administration of scopolamine.

The results of a similar study using the coadministration of the selective 5-HT6 receptor antagonist, Compound 32 and the selective 5-HT2A receptor antagonist, MDL-100907 are shown in FIG. 2. Rats were treated with Compound 32 (1 or 3 mg/kg ip) and/or MDL-100907 (0.1 or 0.3 mg/kg ip) and scopolamine (0.1 mg/kg sc) 30 mins prior to re-release of the animal in an arena containing the familiar object and newly introduced novel object. The time each animal spent investigating the novel and familiar objects in the arena during a over a 3 min interval, commencing 30 minutes after the administration of scopolamine, was scored. The discrimination index (d2) is calculated from (b−a)/(a+b), where a and b are the time spent exploring the familiar and novel objects, respectively. Data were analyzed by Anova. In addition, in order to determine whether an additive effect of 5-HT6 and 5-HT2A receptor blockade exists, the d2 scores in animals treated with 5-HT2A antagonists and/or 5-HT6 antagonist alone or in combination were compared with each other and with within-study controls for animals treated with vehicle or scopolamine only by t-test. Data are presented as means+S.E.M, (* $P<0.05$; ** $P<0.01$). Statistically significant reversal of scopolamine-induced memory impairment were observed for MDL-100907 at 0.3 mg/kg dose and for Compound 32 at 3 mg/kg dose. Even higher levels of reversal of memory impairment were seen in combination treatments of MDL-100907 and Compound 32 at doses of 0.1 mg/kg MDL-100907 and 3 mg/kg Compound 32, and 0.3 mg/kg MDL-100907 and 3 mg/kg Compound 32.

Statistical Analysis

The basic measures were the times spent by rats in exploring an object during T1 and T2. The time spent in exploring the two identical samples will be represented by 'a1' and 'a2'. The time spent in T2 in exploring the sample and new object will be represented by 'a' and 'b', respectively. The following variables were calculated: e1=a1+a2, e2=a+b, h1=e1−e2, d1=b−a and d2=d1/e2 (see Table 1). e1 and e2 are measures of the total exploration time of both objects during T1 and T2 respectively. h1 was considered as an index measure of global habituation of exploratory behavior from T1 to T2. d1 and d2 were considered as index measures of discrimination between the new and the familiar objects. In fact, d2 is a relative measure of discrimination that corrects d1 for exploration activity (e2). Thus, there should be no differences in d2 indices between experiments with similar treatments at similar intervals. However, this need not to be the case for d1 because of differences in exploration activity.

TABLE 2

Measures involved in the object recognition test

| Exploration | Habituation | Discrimination |
|---|---|---|
| e1 = a1 + a2 | h1 = e1 − e2 | d1 = b − a |
| e2 = a + b | | d2 = d1/e2 | e1 is the measure of the time spent in exploring both identical objects (a1 and a2) in the first trial, and e2 is the measure of the time spent in exploring both the familiar (a) and new object (b) in the second trial; hi is the measure of global habituation from trial 1 to trial 2; d1 and d2 are the measures of discrimination between the new and familiar objects.

Example 5

Long Term Potentiation in Rat Hippocampal Slices (CA1)

Long term potentiation (LTP) is a model for learning and memory in the brain. Methods and substances that enhance LTP usually result in improved cognitive function. The purpose of the following experiments was to prepare and record from intact hippocampal slices isolated from rat brain and determine the effects of various compounds on synaptic transmission. Field excitatory postsynaptic potentials (fEPSPs) of CA1 pyramidal neurons were used to study synaptic transmission.

Local regulations on the humane use of laboratory animals were followed. Male rats between the ages of 3 and 6 weeks were used for field potential recordings. Sprague-Dawley rats were obtained from Charles River Laboratories. Animals were anesthetized in a cylindrical anesthesia chamber using 2.5% halothane and oxygenated air for a minimum of 10 minutes.

Slice Preparation

Rats were anesthetized by halothane and decapitated with a guillotine. The brain was removed and placed in ice cold solution (120 mM NaCl, 3.5 mM KCl, 0.7 mM $CaCl_2$, 4.0 mM $MgCl_2$, 1.25 mM $NaH_2PO_4$, 26 mM $NaHCO_3$, 10 mM glucose) bubbled with 95% $O_2$/5% $CO_2$. The same cold solution was used throughout the dissection procedure to prevent transmitter release and minimize injury to the cells, and solution was continuously bubbled with 95% $O_2$/5% $CO_2$ to maintain oxygenation to the brain. The hindbrain was cut away with a straight-edged razor, and the flat surface of the forebrain was glued to the pan of a Leica VT1000E vibratome with cyanoacrylate glue (Loctite). 350 µm slices were cut with the vibratome using low speed and high frequency vibration. The hippocampus was dissected out from each slice with the cortex attached and placed in a chamber containing recording buffer (120 mM NaCl, 3.5 mM KCl, 2.5 mM $CaCl_2$, 1.3 mM $MgCl_2$, 1.25 mM $NaH_2PO_4$, 26 mM $NaHCO_3$, 10 mM glucose) perfused with 95% $O_2$/5% $CO_2$. Slices were allowed to incubate at room temperature in the holding chamber for at least one hour prior to recording.

Electrophysiology

All experiments were performed at room temperature. Individual slices were placed in a submerged recording chamber, held by a net made with flattened platinum wire and nylon threads. Slices were perfused with recording solution (120 mM NaCl, 3.5 mM KCl, 2.6 mM $CaCl_2$, 1.3 mM $MgCl_2$, 1.25 mM $NaH_2PO_4$, 26 mM $NaHCO_3$, 10 mM glucose) saturated with 95% $O_2$/5% $CO_2$, at a rate of 1-2 ml/min.

Schaffer collateral-commissural fibers were stimulated by ultrasmall concentric bipolar electrodes (FHC Inc., Bowdoinham, Me.) delivering 0.1 ms pulses. Stimulus intensities were adjusted to evoke 30-40% maximal responses for normal stimulation. Responses were evoked every 20 seconds, unless otherwise specified.

Pipettes were pulled from borosilicate glass capillaries (type 7052 from World Precision Instruments) with no filament and dimensions of 1.5/1.0, 4 inches in length. The pipettes (3.5-5 MΩ resistance) were filled with a solution containing 120 mM NaCl, 3.5 mM KCl, 2.6 mM $CaCl_2$, 1.3 mM $MgCl_2$, 1.25 mM $NaH_2PO_4$, 26 mM $NaHCO_3$, 10 mM glucose. Pipettes were lowered into the dendritic layer of stratum radiatum and gradually lowered until a sizable response is located.

Recordings were performed using an Axopatch 200 amplifier, filtered at 2 kHz, and analyzed off-line with programs written in Visual Basic and Microcal Origin. The initial slopes of the fEPSPs were measured unless otherwise noted. Data were expressed as mean+/−SEM.

Figure 3:
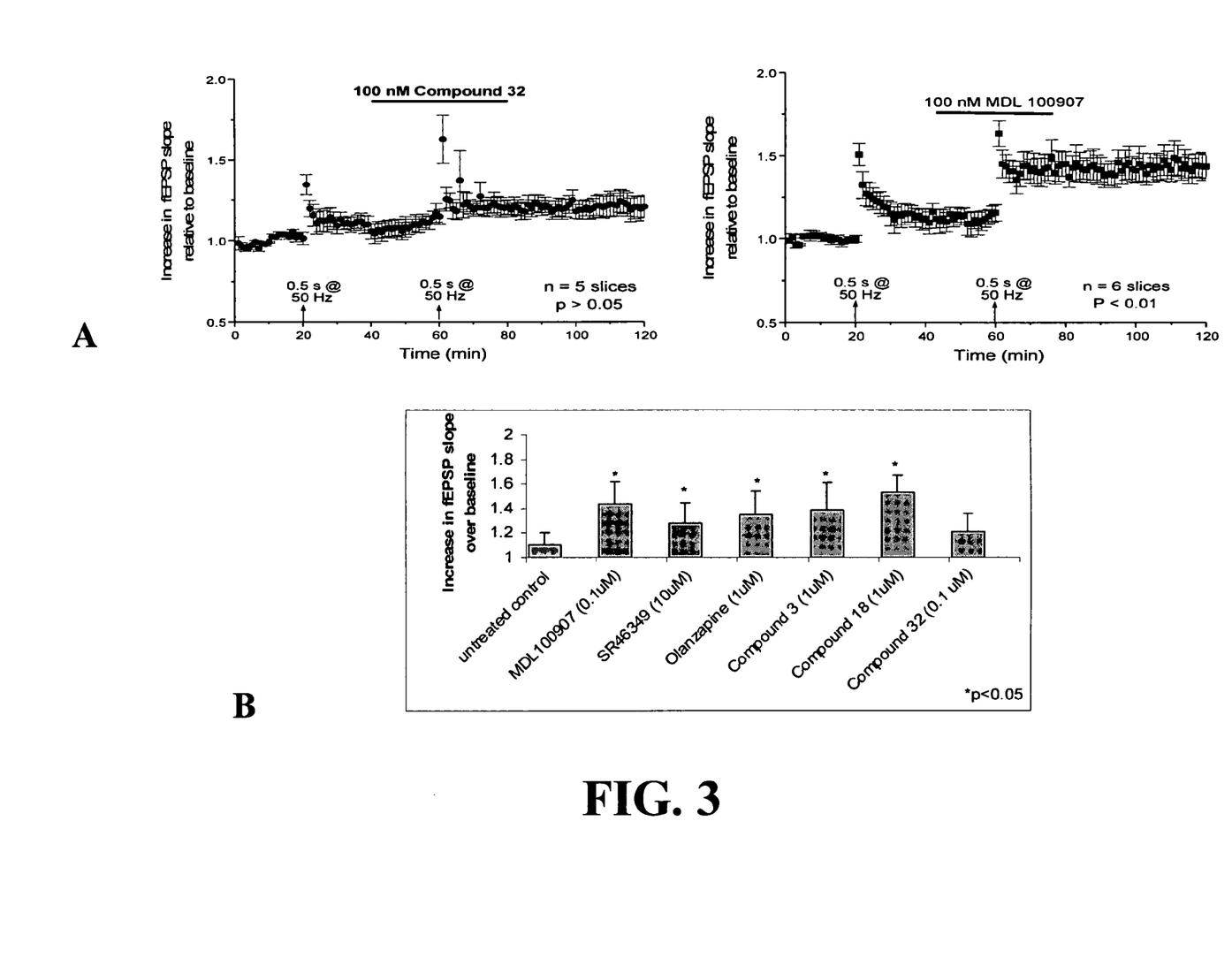
FIG. 3 shows the long term potentiation (LTP) of synaptic signaling in rat brain hippocampal slices (CA1 region). (A) Increase in long term potentiation by MDL100907, but not by Compound 32, shown as increase in slope of field excitatory post-synaptic potentials (fEPSP) relative to pre-tetanus baseline. (B) Mean increase in fEPSP over pre-tetanus baseline in hippocampal slices treated with MDL100907, SR46349, Olanzapine Compounds 3, 18 and 32.

Long-term potentiation (LTP) was induced by a weak tetanus consisting of one train of 50 Hz stimulation lasting 500 ms. Data were normalized to the baseline response before induction of LTP. Compounds were applied following establishment of a stable baseline response. FIG. 3 shows the results of this study represented as current recordings (A) and in a bar chart (B). Increase in long term potentiation by selective 5-HT2A receptor antagonist, MDL-100907, but not selective 5-HT6 receptor antagonist, Compound 32, shown as increase in slope of field excitatory post-synaptic potentials (fEPSP) relative to pre-tetanus baseline (A). Mean increase in fEPSP over pre-tetanus baseline in hippocampal slices treated with MDL-100907, SR46349B, Olanzapine, Compounds 3, 18 and 32 (B). Difference between effect of compound and animal untreated control (determined in slices from same animal) was analyzed by Students t-test. Data are present as mean and S.E.M., * denotes p<0.05. Bar charts in graph B show mean increase in fEPSP slope ~20-40 min after the end of tetanic stimulation.

What is claimed is:

1. A method of treating but not preventing cognitive dysfunction associated with a cognitive disorder comprising administering to a subject in need thereof a therapeutically effective amount of a compound which is a combined selective 5-HT6 receptor/5-HT2A receptor antagonist wherein said compound is selected formula V:

Formula V wherein u is from 0 to 3; v is from 1 to 3; Ar is optionally substituted aryl or optionally substituted heteroaryl; each $R^{16}$ is independently halo, alkyl, haloalkyl, cyano, —$SO_2R^f$, —C(=O)—$NR^gR^h$, —$SR^g$, —C(=O)—$R^g$, where each $R^f$, $R^g$ and $R^h$ is independently hydrogen or alkyl; $R^{17}$ and $R^{18}$ each independently is hydrogen or alkyl, or $R^{17}$ and $R^{18}$ together may form =$NR^i$ wherein $R^i$ is hydrogen or alkyl; $R^{19}$ and $R^{20}$ each independently is hydrogen or alkyl, or one of $R^{19}$ and $R^{20}$ is hydrogen and the other is an optionally substituted heteroaryl, or $R^{19}$ and $R^{20}$ together with the nitrogen to which they are attached may form an amidinyl group, a urea group, a guanidinyl group, or a five- or six-membered ring that optionally includes an additional heteroatom selected from O, N and S, or one of $R^{19}$ and $R^{20}$ and one of $R^{17}$ and $R^{18}$ together with the atoms to which they are attached may form a five- or six-membered ring that optionally includes an additional heteroatom selected from O, N and S; and the pharmaceutically acceptable acid addition salts thereof.

2. The method of claim 1 wherein said compound is selected from the group consisting of:
   (7-Phenylsulfonyl-1,2,3,4-tetrahydro-naphthalen-1-ylmethyl)-(5,5-dimethyl-1,4,5,6-tetrahydro-pyrimidin-2-yl)-amine,
   (6-Phenylsulfonyl-1,2,3,4-tetrahydro-naphthalen-1-ylmethyl)-(4,5-dihydro-1H-imidazol-2-yl)-amine,
   N-(6-Phenylsulfonyl-1,2,3,4-tetrahydro-naphthalen-1-ylmethyl)-guanidine,
   3-(6-Phenylsulfonyl-1,2,3,4-tetrahydro-naphthalen-1-yl)-propionamidine,
   C-(6-Phenylsulfonyl-1,2,3,4-tetrahydro-naphthalen-1-yl)-methylamine,
   (6-Phenylsulfonyl-1,2,3,4-tetrahydro-naphthalen-1-ylmethyl)-methyl-amine,
   N-(6-Phenylsulfonyl-1,2,3,4-tetrahydro-naphthalen-1-ylmethyl)-acetamidine,
   2-[6-(2-Fluoro-phenylsulfonyl)-1,2,3,4-tetrahydro-naphthalen-1-yl]-ethylamine,
   or pharmaceutically acceptable acid addition salts thereof.

3. The method of claim 1 or claim 2 wherein said cognitive disorder is selected from the group consisting of Alzheimer's disease, degenerative disorders associated with learning, learning disabilities, memory or cognitive dysfunction such as mild cognitive impairment, age-related cognitive decline, cerebral senility, vascular dementia, AIDS- associated dementia, electric shock induced amnesia, memoly impairment associated with depression or anxiety, cognitive defects in Parkinson's disease, Down's syndrome, stroke, traumatic brain injury, Huntington's disease, and attention deficit disorder.

4. The method of claim 3 wherein said cognitive disorder is Alzheimer's disease.

* * * * *